United States Patent [19]

Marx

[11] 4,048,991
[45] * Sept. 20, 1977

[54] BRACE APPARATUS

[76] Inventor: Alvin J. Marx, 315 College Road, Bronx, N.Y. 10471

[ * ] Notice: The portion of the term of this patent subsequent to June 7, 1994, has been disclaimed.

[21] Appl. No.: 717,483

[22] Filed: Aug. 25, 1976

Related U.S. Application Data

[63] Continuation-in-part of Ser. No. 617,144, Sept. 26, 1975.

[51] Int. Cl.² .............................................. A61F 13/00
[52] U.S. Cl. ..................................... 128/165; 128/77
[58] Field of Search .................. 128/165, 169, 87, 171, 128/DIG. 15, 77; 2/16; 273/189 R, 189 A

[56] References Cited

U.S. PATENT DOCUMENTS

| | | | |
|---|---|---|---|
| 937,769 | 10/1909 | Collis | 128/169 |
| 2,287,821 | 6/1942 | O'Donovan | 128/169 X |
| 3,256,882 | 6/1966 | Huber | 128/165 |
| 3,536,068 | 10/1970 | Stubbs | 128/169 X |
| 3,877,426 | 4/1975 | Nirschl | 128/165 |

Primary Examiner—John D. Yasko

[57] ABSTRACT

An improved wrist brace maintains the wrist extended and slightly ulnar deviated (so called position of function), providing support and impact counterforce bracing. The brace is utilized for play by sufferers of "tennis elbow" (tendonitis of the conjoined tendon of the extensor communis and extensor carpi radialis brevis at the insertion into the lateral epicondyl of the humerus), reduced subluxation of the wrist ("sprain"), and/or rheumatoid arthritis of the wrist.

The brace includes a semirigid, fluid-passing (e.g., woven) semiflexible outer backer layer, and an inner porous layer, e.g., and open pore plastic. Particular forms of buckle and strapping are secured at opposite ends of the elongated backer-foam laminate to secure the brace in place, as by hook and eye type cooperating fastener strips.

8 Claims, 3 Drawing Figures

BRACE APPARATUS

DISCLOSURE OF THE INVENTION

This invention relates to athletic/medical apparatus and, more specifically, to improved wrist brace apparatus. This invention is a continuation-in-part of my co-pending application Ser. No. 617,144 filed Sept. 26, 1975 the disclosure of which is incorporated herein by reference.

The wrist consists of the eight small bones held tightly by ligaments and arranged in two rows. The proximal row consists of the scaphoid, lunate, triquetrum and pisiform, and the distal row the trapezium, trapezoid, capitate and hamate. The major wrist joints are usually considered to be the articulations between the radius and the proximal row of wrist bones and between the radius and ulna.

At rest the wrist is slightly palmar flexed and ulnar deviated. The wrist's range of motion is 80° flexion, 70° extension, 30° ulnar deviation, and 20° radial abduction.

No muscles insert into the wrist except for the flexor carpi ulnaris which inserts into the pisiform. The usual motions of the wrist are oblique due to antagonistic muscle groups: extensor carpi radialis versus flexor carpi ulnaris.

The arch of the wrist is maintained by the flexor retinaculum which bridges the carpal bones in two bands. The tendons to the deep and superficial flexors of the finger along with the medial nerve are all sandwiched between the ligament and the carpal bones. The radial and ulnar ligaments give strong support to the sides of the wrist. On the palmar surface the bones are held tightly together by the ligament of Henle and others. The dorsal ligaments are fewer and looser.

The radial-carpal joint functions as a universal joint, moving in any direction. The ulna does not articulate with the carpal bones. The radial styloid process is usually distal to the ulnar styloid.

The presence of these bony processes must be taken into consideration when designating a wrist brace. It is not possible to design a wrist bandage to treat all disease processes of the wrist. The instant wrist bracing apparatus is therefore concentrated on the most common conditions that can be treated by mild limitation of motion.

"Tennis elbow" — This condition is the result of a tear in the tendons that insert into the lateral epicondyle of the humerus. These tendons originate in the extensor carpi radialis brevis and the extensor digitorum. The tear usually occurs when the wrist is flexed and these muscles are used as antagonists to the powerful forearm flexors. The subject wrist brace, preferably employed in conjunction with the elbow counterforce brace of the above-identified parent case, used when playing tennis prevents full flexion of the wrist and thereby disallows the tear in the elbow tendon. Once the tear has occurred the subject wrist brace is helpful in preventing further tearing.

Sprain — A "sprain" of the wrist typically result from a trauma (e.g., a fall) on the outstretched hand with the wrist going into hyperextension. Although the pathogenesis of this condition is not well established it appears most likely that the condition is a reduced dorsal subluxation of all the carpal bones of the wrist except for the lunate and proximal part of the scaphoid. Alternative theories are that there is reduced palmer subluxation of the lunate alone or lunate and proximal part of the scaphoid. The subject wrist brace is used in this condition to help support the bones attached to the stretched ligaments, to allow healing and prevent further tearing of already weakened ligaments.

Rheumatoid arthritis — Rheumatoid arthritis affects the distal radio-ulnar joint as well as the radiocarpal joint. If the radiocarpal joint is involved the wrist brace is used to stabilize the wrist. The purpose of treatment is to put the wrist at rest during the acute attack or flare up. Involvement of the radio-ulnar joint can lead to dorsal dislocation of the ulnar head. In far advanced rheumatoid arthritis the hand can go into palmar flexion and ulnar deviation.

It is thus an object of the present invention to provide improved wrist bracing apparatus.

More specifically, it is an object of the present invention to provide wrist bracing structure which limits motion in the wrist. The most effective bracing is upon the radial (thumbside) surface to particularly prevent excess flexion in "tennis elbow" and rheumatoid arthritis. In "sprains" (reduced dorsal subluxation) the brace is applied to prevent flexion or extension.

It is another object of the present invention to provide wrist bracing apparatus which places the wrist into a slight extended ulnar deviated attitude — the so called position of function.

The above and other objects of the present invention are realized in improved semi-flexible wrist bracing apparatus which includes a semi-flexible backer support layer in generally oval form, e.g., formed of a relatively heavy woven canvas. An open pore plastic foam strip is secured to the inner surface and completely covers the inner surface of the semi-flexible backer layer. A buckle and strap of particular configuration are secured at opposite ends of the elongated backing layer-inner foam laminate.

In use, the composite improved brace is very readily slipped over the subject's wrist with the maximum supporting central area of the semi-flexible backer oriented as desired — typically laterally. The degree of support (i.e., resistance to wrist flexation) is increased as desired by moving the brace downward towards the hand. The brace is secured in place by the buckle and strap. The strap loops back upon itself and is secured in place, as by hook and eye (e.g., VELCRO (t.m.) type) mating fastener strips.

The wrist brace so described effects the desired extension — ulnar deviation of the wrist providing the requisite support, trauma counterforcing, and motion resistance.

The above and other features and advantages of the present invention will become more clear from the following detailed description of a specific illustrative wrist brace described herein below in conjunction with the accompanying drawing, in which.

Figure 1:
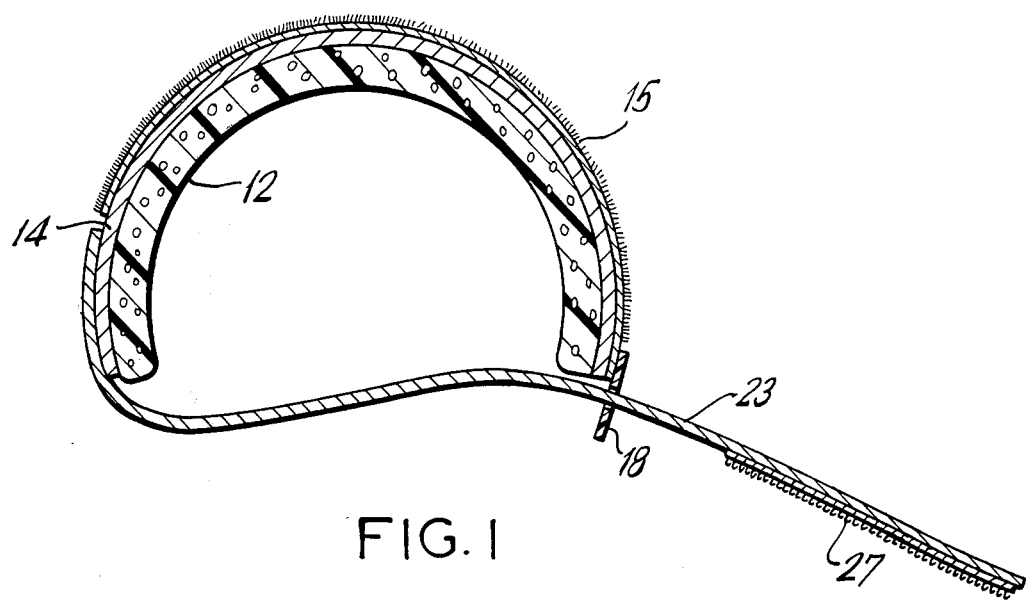
FIG. 1 is a cross sectional view of a semi-flexible wrist brace, in an unapplied orientation.
Figure 1A:
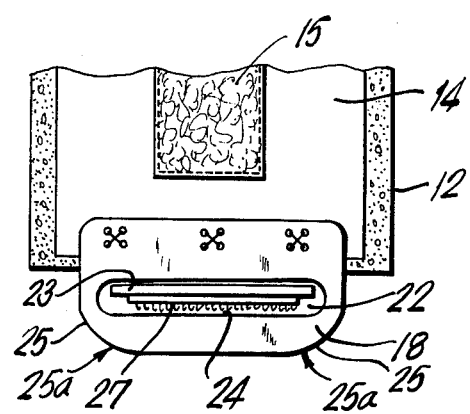
FIG. 1A is a plan view of the loop or buckle end portion of the wrist brace apparatus depicted in FIG. 1.

Referring now to the drawing, there is shown an improved semi-flexible wrist brace illustrating the principles of the present invention, finding general utility for the above-considered "tennis elbow", wrist reduced subluxation or sprain, and/or rheumatoid arthritis conditions. The brace is formed of a semi-flexible rounded, oval-like outer backer layer 14 which includes interstices for ventilation and the elimination of perspiration. The outer semi-flexible backer material may be formed, for example, of a relatively firm woven canvas, e.g., No. 3 canvas approximately ⅛ inch thick. Disposed about the inner surface of the outer layer 14 is a sheet 12 of a relatively soft, fluid (perspiration) passing material such as an open pore urethane foam. The inner foam 12 and outer backing layer 14 are secured together, e.g., by stitching strap which also serves as a perspiration wicking agent to draw fluid in an outwardly radial direction for evaporation after the composite brace has been applied to a subject.

A strap 23 is attached about one end of the laminate 12-14, and may illustratively comprise woven canvas narrower that the width of the laminate and secured thereto, again as by stitching. The closure strap 23 may comprise, for example, No. 2 canvas with a thickness between 1/32 inch and 1/16 inch thick. Secured to the other end of the laminate 12-14 is a semi-flexible buckle 18, preferably secured radially outward from the outer sheet 14, as by stitching. The buckle 18 is formed of a thin plastic, to curve and conform to the wrist when the composite brace has been applied. The buckle 18 includes rounded corners 25, and a closure strap receiving slot 22 near the exposed end thereof, a reinforcing rib 24 being employed about the slot 22 for mechanical integrity. The thin buckle permits ready curvature, about the wrist when the brace is applied — and the ribbing provides the necessary axial resistance for strap 23 fastening.

For fastening purposes mating hook and eye tapes 15 and 27, e.g., those identified by the trademark VELCRO, are respectively affixed to the under portion of the closure strap 23, and about the radially outward surface of the semi-flexible backing element 14.

In practice, the free end of strap 23 is inserted through the slot 22 of the buckle, together with the closure portion 22. The wrist brace is then readily placed upon the wrist over the hand, with the central portion of the laminate 12-14 centered about the portion of the wrist to receive maximum resistance to motion and bias, typically the lateral (thumb) area to extend the wrist with a ulnar deviation into a position of function. The strap 23 is then looped back upon itself and tightened as desired. Finally, the brace is secured in place by engaging the fastener tapes 15 and 27.

Several observations are made at this point. First, the foam inner layer 12 is made wider than the backer canvas 14 to prevent the backer 14 from "biting" into the user's skin causing irritation. To this end, the rounding 25 of the buckle 18 similarly obviates the otherwise pointed corners of the buckle irritating the user, since the transition points 25a of the buckle lie laterally inside the ends of the slot 22, and are spaced from the user by the inner layer of strapping 23. Also, the slot 22 is made only wide enough to accommodate the strap 23, thereby not permitting skin to become "pinched" about the slot area.

Figure 2:
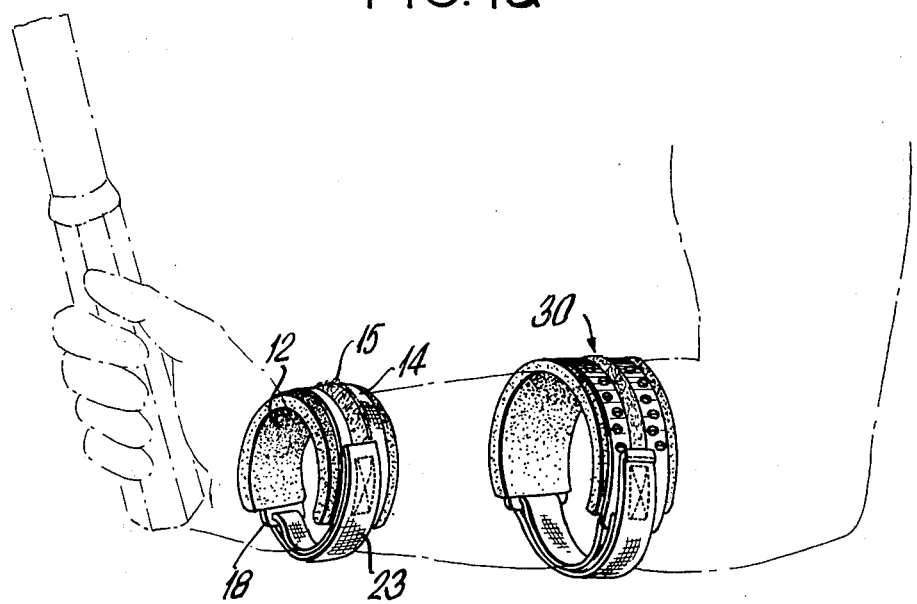
FIG. 2 depicts the bracing apparatus as applied to a subject.

Further, as has been noted, use of the subject wrist brace by those suffering from the "tennis elbow" tendonitis condition will find such tendonitis relieved because of the restricted wrist motion, thereby also restricting stress on the forearm muscles and elbow tendons. However, as in especially useful for such a tennis elbow situation, a forearm brace 30 of the type described in my aforesaid parent application may be employed in conjunction with the instant wrist brace, as shown in FIG. 2. The combined use of the wrist brace and elbow counterforce brace form an especially effective combination for tennis elbow, both prophylactically and to provide symptomatic relief for those already afflicted.

The above described arrangement is merely illustrative of the principles of the present invention. Numerous modifications and adaptations thereof will be readily apparent to those skilled in the art without departing from the spirit and scope of the present invention.

What is claimed is:

1. A brace adapted for application over a subject's wrist comprising an elongated semi-flexible curved backer sheet having a plurality of perspiration eliminating intersticies therein, a porous perspiration passing inner sheet disposed about and secured to the inner surface of said backer means, said semi-flexible backer means being curved in a generally rounded fashion, strap means attached to said semi-flexible curved backer sheet-inner sheet laminate about one end thereof, buckle means affixed to said semi-flexible backer sheet-inner sheet laminate about the other end thereof, said buckle means being adapted to receive the other end of said strap means, and brace securing means comprising mating first and second cooperating portions, said first portion of said mating means being affixed to the outer surface of said strap about its said other end and the second portion of said fastening means being secured to the outer surface of said semi-flexible backer sheet.

2. A combination as in claim 1 wherein said semi-flexible outer backer sheet is formed of a woven canvas.

3. A combination as in claim 2 wherein said porous inner strip means comprises an open pore foam.

4. A combination as in claim 1 wherein said first and second cooperating portions of said securing means respectively comprise hook and eye fastener segments.

5. A combination as in claim 1, further comprising a elbow brace employed about the subject's upper forearm in combination with said wrist brace.

6. A combination as in claim 2, wherein said inner sheet is wider than said backer sheet, wherein said backer sheet is wider than said buckle and said strap means.

7. A combination as in claim 2 further comprising stitching means for securing said buckle means to the outside of said backer sheet, and wherein said buckle means includes a transverse slot, and monotonically tapered front side portions.

8. A combination as in claim 7 further comprising reinforcing rib means disposed on said buckle about said transverse slot therein, and wherein said slot is just long enough to receive said strap means.

* * * * *